United States Patent
Hoofman et al.

(10) Patent No.: US 9,375,711 B2
(45) Date of Patent: Jun. 28, 2016

(54) SENSOR AND A METHOD OF ASSEMBLING A SENSOR

(75) Inventors: Romano Hoofman, Geel (BE); Gerard Reuvers, Eindhoven (NL); Franciscus Petrus Widdershoven, Eindhoven (NL); Evelyne Gridelet, Omal (BE); Marcus Henricus van Kleef, Nijmegen (NL)

(73) Assignee: NXP B.V., Eindhoven (NL)

( * ) Notice: Subject to any disclaimer, the term of this patent is extended or adjusted under 35 U.S.C. 154(b) by 37 days.

(21) Appl. No.: 13/043,352

(22) Filed: Mar. 8, 2011

(65) Prior Publication Data
US 2011/0217206 A1 Sep. 8, 2011

(30) Foreign Application Priority Data
Mar. 8, 2010 (EP) ...................................... 10155825

(51) Int. Cl.
*G01N 27/00* (2006.01)
*B01L 3/00* (2006.01)
*G01N 27/327* (2006.01)

(52) U.S. Cl.
CPC ...... *B01L 3/502715* (2013.01); *G01N 27/3275* (2013.01); *B01L 2200/12* (2013.01); *B01L 2300/0645* (2013.01); *Y10T 29/49105* (2015.01)

(58) Field of Classification Search
CPC .......... G01N 27/4146; G01N 27/3272; G01N 27/9033
USPC ......... 422/563, 561, 560, 82.03, 82.01, 82.02
See application file for complete search history.

(56) References Cited

U.S. PATENT DOCUMENTS

| | | |
|---|---|---|
| 2004/0228770 A1 | 11/2004 | Gandhi et al. |
| 2005/0031490 A1 | 2/2005 | Gumbrecht et al. |
| 2005/0106742 A1 | 5/2005 | Wahl |
| 2008/0148861 A1 | 6/2008 | Beer |
| 2009/0029477 A1* | 1/2009 | Meller et al. ..................... 436/94 |
| 2009/0051052 A1 | 2/2009 | Yoshioka et al. |
| 2010/0089135 A1 | 4/2010 | de Langen |

FOREIGN PATENT DOCUMENTS

| | | |
|---|---|---|
| WO | 02/072264 A1 | 11/2002 |
| WO | 2010/041225 A1 | 4/2010 |

OTHER PUBLICATIONS

P. Krulevitch et al., "Polymer-Based Packaging Platform for Hybrid Microfluidic Systems," Biomedial Microdevices, vol. 4, No. 4. pp. 301-308, (Dec. 1, 2002).

(Continued)

*Primary Examiner* — Natalia Levkovich

(57) ABSTRACT

"Click-assembly" methods of assembling a sensor for sensing biologically-active molecules by measuring impedance changes, are disclosed, comprising supporting a bio-sensor on a carrier, the bio-sensor comprising an electronic component having at least one micro-electrode and at least one electrical contact, functionalizing the bio-sensor by physically or chemically coupling a bio-receptor molecule to each of the at least one micro-electrode, and subsequently assembling the bio-sensor with a micro-fluidic unit by means of a clamp which clamps the bio-sensor with the micro-fluidic unit, such that in use a fluid introduced into the micro-fluidic unit is able to contact the bio-receptor and is isolated from the electrical contact. The clamp may be a spring, and the method may avoid a requirement for sealing by chemical or thermal means and thereby avoid damaging the bio-receptor.
Sensors which can be assembled according to such methods are also disclosed.

17 Claims, 3 Drawing Sheets

(56) References Cited

OTHER PUBLICATIONS

B. L. Gray et al., "Interlocking Mechanical and Fluidic Interconnections for Microfluidic Circuit Boards," Sensors and Actuators A, vol. 112, No. 1, pp. 18-24, (Apr. 15, 2004).

M Jager et al., "Impedance Measurements in Cell Cultures on Polymer Slides," 1st Electronics Systemintegration Tech. Conf. IEEE, pp. 1203-1208 (Sep. 5, 2006).

Extended European Search Report for European Patent Appln. No. 10155825.2 (Jul. 20, 2010).

* cited by examiner

SENSOR AND A METHOD OF ASSEMBLING A SENSOR

CROSS-REFERENCE TO RELATED APPLICATIONS

This application claims the priority under 35 U.S.C. §119 of European patent application no. 10155825.2, filed on Mar. 8, 2010, the contents of which are incorporated by reference herein.

1. Field of the Invention

This invention relates to sensors and methods of assembling sensors.

2. Background of the Invention

Silicon sensor and biosensor chips have been developed for detection of specific molecules or bio-molecules, such as deoxyribonucleic acid (DNA) or proteins, which is of great interest in the field of medical diagnostics.

A biosensor may be denoted as a device which may be used for the detection of an analyte and may combine a biological component with a physicochemical or physical detector component. For instance a biosensor may be based on the phenomenon that capture particles immobilised on the surface of a sensor, may selectively attach with target particles in a fluidic sample, for instance when an antibody-binding fragment of an antibody or the sequence of a DNA single strand as a capture particle fits to a corresponding sequence or structure of a target particle. When such attachment or sensor event occurs at the sensor, this may change the electrical properties of the surface, which change can be detected as the sensor event.

Biosensors are typically packaged as disposable cartridges, which are inserted into sensor measurement devices to extract information from the sensor chips. A conventional sensor measurement device includes components to support a sensor cartridge with a biosensor, to supply a fluid to the biosensor and to electrically connect to the biosensor to exchange information with the biosensor.

In order to activate a biosensor, its sensor surface may need to be functionalised, that is to say, a molecule (a receptor molecule, also referred to as a bio-receptor) which can bind to the biologically active target molecule, needs to be bonded to the sensor surface. This functionalization typically involves dipping the sensor for several hours in chemical solvents. The functionalization can be done either inside the cartridge or before the sensor is integrated into the cartridge.

Functionalization inside the cartridge is not straightforward since the chemicals used for functionalization might interact with the materials of the microfluidic cartridge; moreover it is only practical to functionalize the sensor area with one receptor molecule, since spotting on the sensor in order to make it able to detect several kind of bio-molecules is not possible.

Functionalization of the biochips before integration inside the microfluicics is not straightforward as well, since these molecules generally cannot withstand elevated temperatures or exposure to solvents. Therefore standard packaging/assembly techniques can not be used.

There is an ongoing need to provide a method of assembling a sensor which does not suffer, or suffers only to a lesser extent, from the above difficulties.

SUMMARY OF THE INVENTION

It is an object of the present invention to provide a method of assembling a sensor which does not suffer from, or suffers only to a lesser extent, from the above difficulties. It is a further object of the present invention to provide a sensor.

According to the invention there is provided a method of assembling a sensor for sensing biologically-active molecules by measuring impedance changes, the method comprising supporting a bio-sensor on a carrier, the bio-sensor comprising an electronic component having at least one micro-electrode and at least one electrical contact, functionalizing the bio-sensor by physically or chemically coupling a bio-receptor molecule to each of the at least one micro-electrode, and subsequently assembling the bio-sensor with a micro-fluidic unit by means of a clamp which clamps the bio-sensor with the micro-fluidic unit, such that in use a fluid introduced into the micro-fluidic unit is able to contact the bio-receptor and is isolated from the electrical contact. By means of such a method, which may be colloquially termed as "click-and-go", the sensor may be assembled without the use of high temperature processing or use of chemically aggressive materials, such as is commonly found in the field of electronic packaging. By avoiding high temperatures and use of reactive chemicals, and damage to the sensitive functionalised active sensor area may be avoided, thereby facilitating the functionalisation of the sensor prior to the sealing of the biosensor to the microfluidic unit.

In embodiments, the clamp comprises a spring which urges the micro-fluidic unit towards the carrier. A spring provides the convenient form of the clamp; for instance, of the components and may yet thereby be detachable a fixed in appropriate cases. Moreover, assembly is simplified by use of a spring, relative to use of other clamping means, since typically no final adjustment is required.

In embodiments, (c) includes forming a liquid-tight seal between the micro-fluidic unit and the bio-sensor, which liquid-tight seal is produced by pressure provided by the spring.

In embodiments, (c) includes providing a spacer between micro-fluidic unit and the carrier as at least part of the liquid-tight seal. In particular embodiments (c) includes providing a flex-foil between the bio-sensor and the carrier, the flex-foil being at least part of the liquid-tight seal and having at least one electrical conductor and being for, in use, making electrical connection with the biosensor.

In embodiments, (c) is achieved solely by mechanical means. Entirely avoiding the use of high temperatures, or chemical means such as adhesives in contact with the electrodes, may assist in preventing damage to the sensitive functionalised active region.

According to another aspect of the present invention, there is provided a sensor for sensing a biologically-active molecule by measuring impedance changes, the bio-sensor device comprising a bio-sensor on a carrier, a micro-fluidic unit, and a clamp, wherein the biosensor comprises an electrical component having at least one micro-electrode and at least one electrical contact and being functionalized by the provision of a bio-receptor on the at least one micro-electrode, the clamp being for clamping the micro-fluidic unit with the carrier such that in use a fluid introduced into the micro-fluidic unit is able to contact the bio-receptor and is isolated from the electrical contact.

In embodiments, the clamp comprises a spring for urging the micro-fluidic unit towards the carrier.

In embodiments, the sensor further comprises a spacer, between the carrier and the micro-fluidic unit.

In embodiments, the sensor further comprises a flex-foil for making electrical connection with the electrical contact. In particular embodiments, the flex-foil is integral with the micro-fluidic unit. The flexfoil may comprise at least one finger having a deformable bump at its tip, the bump being of an electrically-conducting material and arranged to be urged against the electrical contact by means of the clamp and for making electrical connection to the electrical contact.

In embodiments, the sensor further comprises a needle which is arranged to be urged against the electrical contact and for making electrical connection to the electrical contact.

In embodiments the micro-fluidic unit comprises a plurality of components. Alternatively, the microfluidic unit may be formed from a single component, the microfluidic channel or channels being formed therein by known processes.

In embodiments wherein there are a plurality of components forming the microfluidic unit, the plurality of components may be configured to auto-align with the biosensor during assembly, by means of any of at least one of lugs, spigots, grooves or other geometrical features on at least one of the components.

In embodiments, the spring is a generally n-shaped clip having a top and walls, the carrier is located generally within the clip and between the top and the bio-sensor, and the walls have at least one of protrusions and depressions for engaging the micro-fluidic unit.

These and other aspects of the invention will be apparent from, and elucidated with reference to, the embodiments described hereinafter.

BRIEF DESCRIPTION OF DRAWINGS

Embodiments of the invention will be described, by way of example only, with reference to the drawings, in which.

Figure 1A:
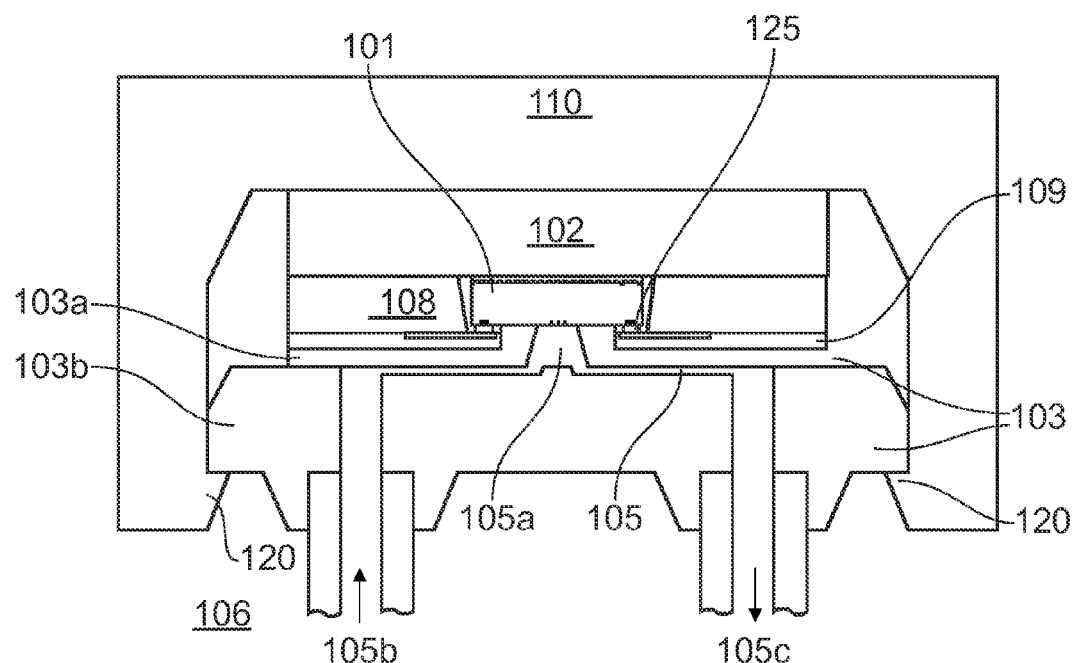
FIG. 1(a) shows a schematic cross-section through a bio-sensor cartridge, according to an embodiment of the invention.

It should be noted that the Figures are diagrammatic and not drawn to scale. Relative dimensions and proportions of parts of these Figures have been shown exaggerated or reduced in size, for the sake of clarity and convenience in the drawings. The same reference signs are generally used to refer to corresponding or similar feature in modified and different embodiments

DETAILED DESCRIPTION OF EMBODIMENTS

As used herein, the term "biosensor" may denote any device which may be used for the detection of a component of an analyte comprising biological particles such as DNA, Ribonucleic acid (RNA), proteins, enzymes, cells, bacteria, virus, etc. A biosensor may combine a biological component (for instance capture particles at a sensor active surface capable of detecting particles) with a physicochemical or physical detector component (for instance a capacitor having an electric characteristic which is modifiable by a sensor event).

The term "sensor chip" may particularly denote that a sensor built with the help of micro- or nano-technologies such as lithography, etch or deposition techniques. It may particularly denote an integrated circuit (IC), that is an electronic chip, particularly in semiconductor technology, more particularly in silicon semiconductor technology, still more particularly in complementary metal oxide semiconductor (CMOS) technology. A monolithically integrated sensor chip has the property of having very small dimensions due to the use of micro- or nano-processing technology, and may therefore have a large spatial resolution and a high signal-to-noise ratio particularly when the dimensions of the sensor chip or more precisely of components thereof approach or reach the order of magnitude of micrometers or less, for instance, a sensor reaching the dimensions of biological particles.

The term "fluidic" may particularly denote any subset of the phases of matter. Such fluids may include liquids, gases, plasmas and, to some extent, solids, as well as mixtures thereof. Examples for fluidic samples are DNA containing fluids, cells containing fluids, blood, interstitial fluid in subcutaneous tissue, muscle or brain tissue, urine or other body fluids. For instance, a fluidic sample may be a biological substance. Such a substance may comprise proteins, polypeptides, nucleic acids, DNA strands, etc.

The term "particle" may particularly denote a molecule, an organic molecule, a biological particle, DNA, RNA, a protein, an amino acid, a bead, a nano-bead, a nano-tube, etc.

The term "biological particles" may particularly denote any particles which play a significant role in biology or in biological or biochemical procedures, such as genes, DNA, RNA, proteins, enzymes, cells, bacteria, virus, etc.

FIG. 1(a) shows a schematic cross-section through a biosensor cartridge, according to an embodiment of the invention. The figure shows a biosensor chip 101, which is supported on a carrier 102. The biosensor chip 101 is in contact with a microfluidic unit 103, which comprises two parts, a first part 103a and a second part 103b, there being a fluidic channel 105 between the two parts. First part 103a of the microfluidic unit has an aperture adjacent the biosensor chip, such that the microfluidic channel 105 enables fluid to contact the chip at the location 105a. Microfluidic channel includes inlet 105b and outlet 105c, at inlet and outlet pipes or tubes 106 and 107 respectively. Between the carrier 102 and the microfluidic unit 103, is a spacer 108, and a flex-foil 109. As will be familiar to the person skilled in art, a flex foil is a flexible foil made of a polymeric material. The polymeric material is electrically insulating. Either on the surface or embedded in the polymeric material, are one or more electrically conducting tracks, which are typically of copper or another good electrical conductor. The flex-foil provides for a plurality of electrical connections to the biosensor 101 by means of solder contacts 125, or gold bumps, or other means, all of which will be immediately apparent to the skilled person. The electrical connections are isolated from each other by the polymeric material.

The cartridge includes a spring 110, which as shown may partially or generally surround at least some of the other components. In the embodiment shown in FIG. 1(a), the spring 110 is configured as a clip, which is located around the biosensor on its carrier, and engages with the microfluidic unit.

The spring 110 is configured to urge the microfluidic unit against the biosensor chip on its carrier. In the embodiment shown, the clip is of a generally n-shaped configuration, having a top plate and walls. At their lower ends, the walls are each provided with lugs, or protrusions, 120, which engage with an outer base of the microfluidic unit 103 in order to urge the microfluidic unit to also see a biosensor on its carrier. The lugs may extend along the full extent of the walls, or only partly along the walls; in the later case there may be more than one lug on a wall. In other embodiments, the clip may be provided with depressions in the inner face of its one of more of its walls, and the microfluidic unit may be engaged therein. Irrespective of its precise configuration, the function of the clip is to provide a force which urges the microfluidic unit against or towards the biosensor.

Figure 1B:
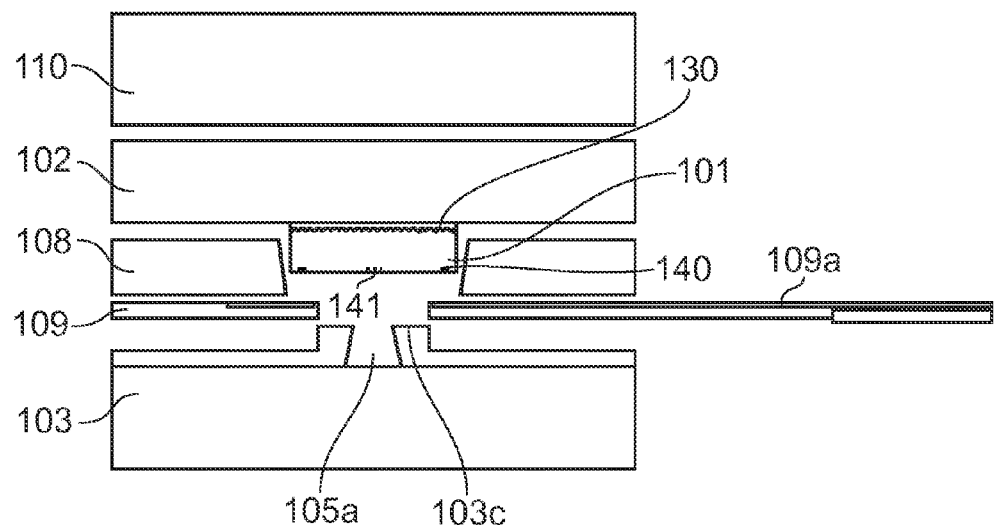
FIG. 1(b) shows a cross-section of the same biosensor cartridge, in a direction orthogonal to that of FIG. 1(a)

FIG. 1(b) shows a cross-section of the same biosensor cartridge, in a direction orthogonal to that of FIG. 1(a); the view shown in FIG. 1(b) is slightly exploded, to more clearly show five distinct parts or components of which the cartridge is comprised. Starting with the topmost component shown in FIG. 1(b), there is shown the spring clip 110. As shown in this embodiment, the clip does not have any legs or walls on the visible faces. That is to say, in this embodiment the clip has walls connected to two, opposite, sides of its top, but not on the other two sides. In other embodiments, the clip may have walls on one or other of these sides, in addition or alternatively to those shown in FIG. 1(a).

Shown below the clip 110 is the carrier 102 with the chip 101 thereon. In an embodiment (not shown), the carrier may be defined in an asymmetric shape to help with the alignment when the cartridge is assembled. The size of the carrier is selected so that it can be easily handled by hand or with a tweezer. As an example, the size of the biosensor chip 101 may be $2\times 2$ mm$^2$ and the size of the carrier may be $10\times 20$ mm$^2$. Reference numbers, alignment marks and other features (not shown in the figure) may be defined on the carrier, as may other additional features, such as fiducials, to assist in accurate placement of the biosensor on the carrier or the assembly of the cartridge.

As shown in FIG. 1(b), the biosensor 101 is attached to the carrier 102, typically by means of an adhesive layer 130. Epoxy glue or other suitable glue may be used for this purpose. The glue should be chemically resistant and inert, in that it should not be affected by subsequent functionalization of the biosensor, which will be considered in more detail below. By fixedly mounting the relatively small biosensor on to the relatively large carrier, handling thereof may be significantly simplified. In particular, despite the fact that the biosensor chip is not packaged according to well-known conventional electronic packaging methods which will be familiar to those experienced in the field of semiconductor processing, once mounted on the carrier the chip may be readily handled by chemists and biochemists who are not experienced in the field of semiconductor packaging and are not used to handling bare semiconductor die. In particular the chip, once mounted on the carrier, may be treated like a conventional component for chemical assay or high-throughput screening or analysis. Returning to FIG. 1(b), the spacer layer 108 is shown generally between the carrier 102 and the microfluidic unit 103. The spacer layer may be useful in helping to locate and retain either or both the biosensor 101 and the flex-foil 109 relative to the microfluidic unit 103.

Underneath the spacer layer, and extending laterally so as to be partly directly beneath the biosensor 101, is the flexfoil 109, and as shown the flexfoil includes thereon the electrical conducting tracks 109*a*. Although the flexfoil extends underneath the biosensor chip, it only extends under the edge regions in order to make electrical connection with the electrical contacts 140 of the biosensor, and does not extend under the, generally central, active sensing area.

Underneath the flexfoil is the microfluidic unit 103. Channel 105 is not generally shown in this figure, however the part 105*a* of the channel which allows fluid into contact with the biosensor 101 is shown. In this embodiment, the microfluidic unit 103 has a top surface 103*c* which, once the assembly is compressed by means of the spring 110, will be in direct contact with the biosensor chip, to form a liquid tight seal therebetween. The liquid tight seal prevents leakage of the analyte, and in particular prevents the analyte making contact with the electrical contacts 140. The opening 105*a* in the fluid channel is positioned relative to the biosensor 101, in order to ensure that nanoelectrodes 141, which provide the sensing surface of the biosensor, are exposed to the analyte fluid.

As shown in this embodiment, the microfluidic unit 103 forms the liquid tight seal by means of the flat surface 103*c*. In other embodiments (not shown), the seal may be formed by a knife-edge which may be deformable, or partially deformable, instead of mating surface 103*c*.

Figure 2:
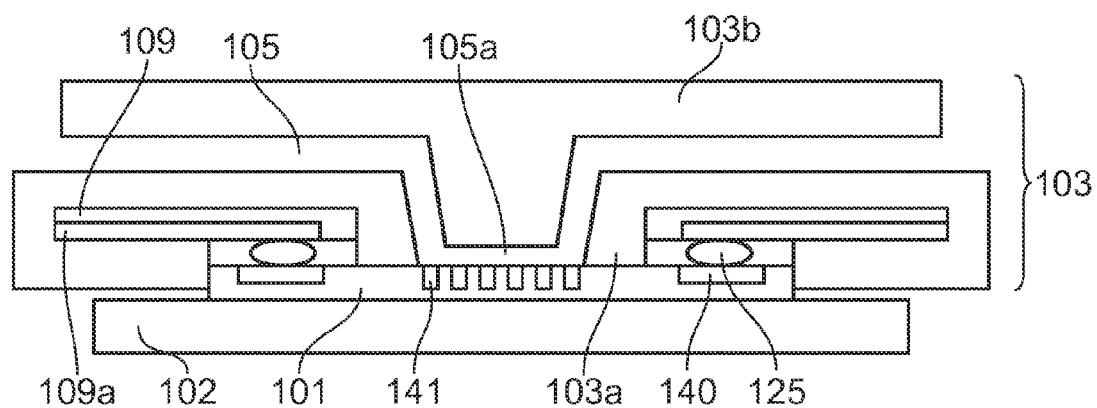
FIG. 2 shows a schematic cross-section through part of another biosensor cartridge.

FIG. 2 shows a schematic cross-section through part of a biosensor cartridge according to another embodiment of the invention. This shows part of the cartridge assembly, omitting the spring or clip 110. This partial assembly is shown inverted with respect to that shown in FIG. 1. The microfluidic unit comprises a first and second part 103*a* and 103*b* respectively. In this embodiment, the flexfoil 109 is shown imbedded in part 103*a* of the microfluidic unit. As shown, the flexfoil 109 includes electrical tracks 109*a*. In other embodiments (not shown) the tracks may be directly formed within or on the microfluidic unit without requiring a separate flexfoil. In the embodiment shown, the electrical tracks on the flexfoil make electrical connection with the electrical contacts 140 of the biosensor chip 101 by means of low-temperature solder joints 125. Alternative connection means such as gold bumps may be used. Particularly convenient are permanent mechanical bonds, such as room-temperature curing electrical adhesives. Also shown are nanoelectrodes 141 of the biosensor, which are aligned with the region 105*a* of the fluid channel 105 within the microfluidic unit 103, whereat the analyte is to be brought into contact with the sensor surface of the biosensor 101. A printed circuit board may be used instead of a flex-foil. The flex-foil may be inserted in the microfluidic part, for instance during moulding or injection moulding of the microfluidic part. An adhesive or a tape (anisotropic conductive tape for example) may be used to improve the electrical connection between the sensor and the flex-foil.

Figure 3:
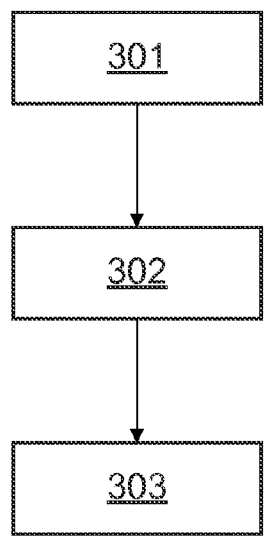
FIG. 3 shows the flow diagram of a process for assembling a sensor.

FIG. 3 shows a flow diagram of for the process of assembling a sensor. In a first process step 301, the biosensor 101 is fixedly attached to the carrier 102, as described above, typically by means of a suitable adhesive.

In a second step 302, the biosensor is functionalised. The biosensor 101 includes a detection area, whereat in use a fluid containing a biological sample will be applied to the biosensor and allowed to flow, to detect any biomolecules contained therein. The detection area is formed of an array of the nanoelectrodes 141; the detection area may typically have an area which is less than 1 mm×1 mm, for example, it may be 150 μm by 185 μm. To functionalize the biosensor, the nanoelectrodes 141 are coated with a functionalization layer 310, typically a self-assembled monolayer, which is deposited in an organic solvent. The specificity of the biosensor 101 is obtained by attaching to the functionalization layer, known probe biomolecules, such as a complementary DNA strand of a target DNA strand for example that can specifically attach to target biomolecules, such as the target DNA strand for example. A measurement of the biosensor 101 results in the detection of the attachment of the target biomolecule to the probe biomolecule. In some embodiments, several types of known probe biomolecules may be deposited on different areas of the functionalization layer to detect several different types of target biomolecules in the detection area of the biosensor 101. The deposition of one or more types of probe biomolecules may be advantageously be performed during this functionalization stage. It should be noted that once the biosensor 101 has been functionalised, care has to be taken in subsequent processing in order to avoid damaging the probe molecule or other parts of functionalised device. In particular, once functionalised, the biosensor on its carrier should not be subjected to significantly elevated temperatures, since the probe molecules cannot withstand such high temperatures as would normally be used in no conventional electronic packaging and assembly processes.

In a third process step 303, the cartridge is assembled. This process step involves accurately aligning the biosensor on its carrier with the microfluidic unit 103, and in embodiments where there is a separate flexfoil, with the flexfoil 109. Alignment lugs, tags, holes or other fiducials may be provided on one or more of the components in order to assist with the alignment. The microfluidic unit is then urged against the biosensor on its carrier, by means of spring 110, which in the embodiment shown above takes the form of a clip.

This process step results in a, at least substantially, liquid-tight seal between the biosensor and the microfluidic unit. Depending on the application, it may be necessary for the liquid tight seal to be a hermetic seal, or it may be allowable for there to be a small amount of seepage, provided that damage is not thereby caused to the device. Furthermore, the seal may be provided directly between the microfluidic unit and the biosensor chip; in other embodiments (not shown), the flexfoil may form part of the seal. This has the advantage that the flexfoil, being formed other polymeric material, may be designed to be at least to some extent deformable, the deformation serving to enhance the seal. Furthermore, in other embodiments (again not shown), the spacer may be utilised to form a part of the seal. Such embodiments are advantageous, in that the material for spacer may be any of a wide range of materials, and chosen so as to be particularly suited to forming an effective seal.

Figure 4A:
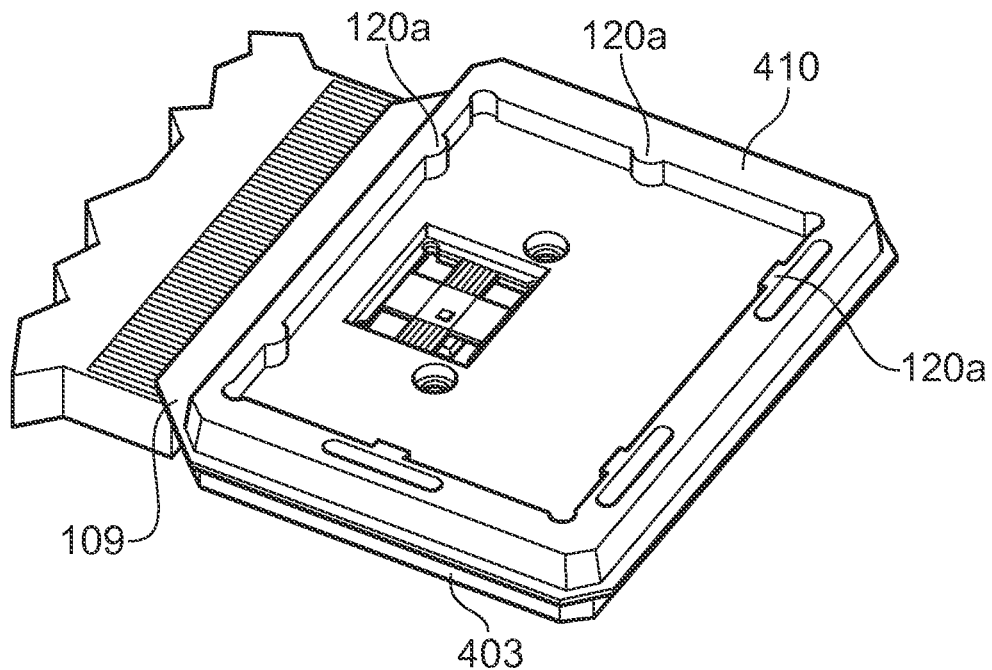
FIG. 4(a) shows part of a biosensor cartridge prior to assembly.
Figure 4B:
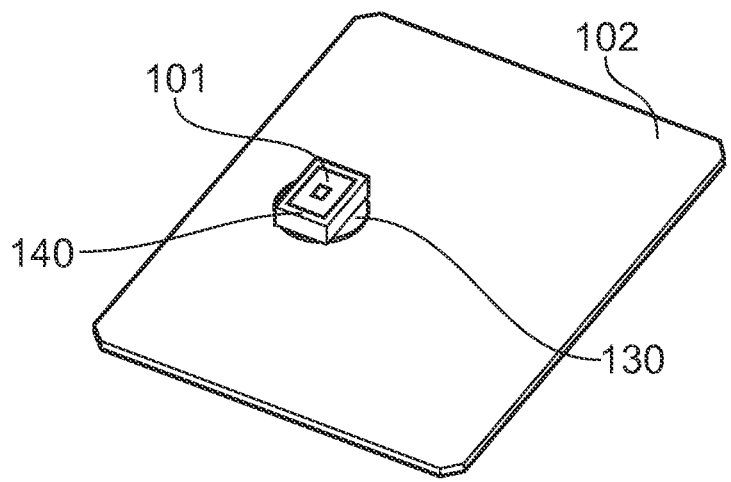
FIG. 4(b) shows a biosensor chip mounted on a carrier prior to assembly with the part shown in FIG. 3(a).

Turning to FIG. 4, FIG. 4(a) shows part of a biosensor cartridge prior to assembly; and FIG. 4b) shows a biosensor chip mounted on a carrier prior to assembly with the part shown in FIG. 4(a). In this embodiment, the flexfoil is assembled together with a microfluidic unit of 403, and an upper housing 410. The upper housing 410 includes a recess, into which the carrier 102 may be inserted. On one or more sidewalls of the recess are protrusions or lugs 120a. In the base of the recess in the upper housing 410 is a through-hole which provides access to the flexfoil, in particular to the electrical tracks in the flexfoil, and to the region at 105a of the channel 105 (not shown) in the microfluidic unit 403. FIG. 4a shows the partial assembly, prior to locating the biosensor 101, mounted on its carrier 102, into the recess. FIG. 4b shows the chip mounted on the carrier 102 by means of adhesive 130, ready for locating and assembly into the recess. In the embodiment, the adhesive 130 may be rigid; however, in other embodiments, the adhesive may be semi-flexible, in order to provide for independent alignment of the biosensor 101, with the microfluidic unit, on the assembly of the carrier into the recess in the holder of 410. As shown, the biosensor 101 may be located offset from the centre of the carrier 102, in order to prevent mis-assembly in the wrong relative orientation.

On assembly of the biosensor 101 and the carrier 102 into the recess of the upper housing 410, the lugs 120a may act to locate the carrier and/or the bio-sensor laterally. In addition, the lugs may be shaped so as to urge the carrier downwards towards the microfluidic unit. For instance, the lugs may be thicker towards the top of the upper housing than towards the bottom of the recess, thereby providing, on assembly, a downwards pressure on the carrier 102. In this embodiment, the lugs form the springs 110. In other embodiments, a separate spring, such as one or more C-shaped clips, may be provided in order to urge the carrier towards the microfluidic unit.

In other embodiments, a different form of mechanical clamp may be used, instead of a spring. For instance, screws or bolts may be used instead of lugs in order to urge the carrier towards the microfluidic unit. The clamp may provide a removable fixing or a permanent fixing. For instance, in embodiments where the clamping function is provided by means of screws, these may be tightened and then sealed into position, by means of a suitable sealant or adhesive.

The clamp may clamp the biosensor directly to the microfluidic unit, such that they are in direct and immediate contact; in other embodiments of the clamp may clamp the biosensor only indirectly to the microfluidic unit with one or more other components, such as the flexfoil or spacer layer, the therebetween. In any case, the biosensor is clamped with the microfluidic unit.

In summary, then, from one viewpoint, "click-assembly" methods of assembling a sensor for sensing biologically-active molecules by measuring impedance changes, are disclosed hereinabove, comprising supporting a bio-sensor on a carrier, the bio-sensor comprising an electronic component having at least one micro-electrode and at least one electrical contact, functionalizing the bio-sensor by physically or chemically coupling a bio-receptor molecule to each of the at least one micro-electrode, and subsequently assembling the bio-sensor with a micro-fluidic unit by means of a clamp which clamps the bio-sensor with the micro-fluidic unit, such that in use a fluid introduced into the micro-fluidic unit is able to contact the bio-receptor and is isolated from the electrical contact. The clamp may be a spring, and the method may avoid a requirement for sealing by chemical or thermal means and thereby avoid damaging the bio-receptor. Sensors which can be assembled according to such methods have also been disclosed.

From reading the present disclosure, other variations and modifications will be apparent to the skilled person. Such variations and modifications may involve equivalent and other features which are already known in the art of biosensors, and which may be used instead of, or in addition to, features already described herein.

Although the appended claims are directed to particular combinations of features, it should be understood that the scope of the disclosure of the present invention also includes any novel feature or any novel combination of features disclosed herein either explicitly or implicitly or any generalisation thereof, whether or not it relates to the same invention as presently claimed in any claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable sub-combination.

The applicant hereby gives notice that new claims may be formulated to such features and/or combinations of such features during the prosecution of the present application or of any further application derived therefrom.

For the sake of completeness it is also stated that the term "comprising" does not exclude other elements or steps, the term "a" or "an" does not exclude a plurality, and reference signs in the claims shall not be construed as limiting the scope of the claims.

The invention claimed is:

1. A sensor for sensing a biologically-active molecule by measuring impedance changes, the sensor comprising:
   a bio-sensor affixed to a carrier having a structure that supports the bio-sensor,
   a micro-fluidic unit including surfaces that define a fluid channel and having a fluid contact location adjacent to a portion of the bio-sensor, and
   a clamp,
   wherein the bio-sensor comprises an electrical component having at least one nanoelectrode and at least one electrical contact electrically connected to the nanoelectrode and being functionalized by the provision of a bio-receptor on the at least one nanoelectrode,
   the clamp being for clamping the micro-fluidic unit with the carrier such that in use a fluid introduced into the micro-fluidic unit is able to contact the bio-receptor, at the fluid contact location, and is isolated from the electrical contact.

2. A sensor according to claim 1, wherein the clamp comprises a spring for urging the micro-fluidic unit towards the carrier.

3. A sensor according to claim 1,
   wherein the micro-fluidic unit further defines an open channel,
   further comprising a spacer, between the clamp and the micro-fluidic unit, including a cavity configured and arranged to enclose the biosensor with the nanoelectrodes of the biosensor directly over the open channel.

4. A sensor according to claim 1, further comprising a flex-foil for making electrical connection with the electrical contact.

5. A sensor according to claim 4, wherein the flex-foil is integral with the micro-fluidic unit.

6. A sensor according to claim 4 wherein the flex-foil comprises at least one finger having a deformable bump at its tip, the bump being of an electrically-conducting material and arranged to be urged against the electrical contact by means of the clamp and for making electrical connection to the electrical contact.

7. A sensor according to claim 1 further comprising a needle which is arranged to be urged against the electrical contact and for making electrical connection to the electrical contact.

8. A sensor according to claim 1, wherein the micro-fluidic unit comprises a plurality of components.

9. A sensor according to claim 8, wherein the plurality of components are configured to auto-align with the biosensor during assembly, by means of any of at least one of lugs, spigots, grooves or other geometrical features on at least one of the components.

10. A sensor according to claim 2, wherein the spring is a generally n-shaped clip having a top and walls, the carrier is located generally within the clip and between the top and the bio-sensor, and, optionally, the walls have protrusions for engaging the micro-fluidic unit.

11. A sensor according to claim 1, wherein the bio-sensor includes the bio-receptor, the bio-receptor being coupled to the nanoelectrode and configured and arranged to
   chemically interact in response to contact with a target molecule at the fluid contact location, and
   impart a detectable electrical characteristic, to the nanoelectrode, that is indicative of the chemical interaction with the target molecule.

12. A sensor according to claim 1, wherein the at least one electrical contact is separated from the nanoelectrode by a first distance, further including a conductive connector that electrically connects the at least one electrical contact to the nanoelectrode, the sensor including a material that isolates the at least one electrical contact from the fluid.

13. An apparatus comprising:
   a micro-fluidic structure having sidewalls that define a fluidic channel;
   a bio-sensor configured and arranged with the micro-fluidic structure to form a cavity in which the fluid flows via the fluidic channel, the bio-sensor including
      a nanoelectrode, and
      a bio-receptor coupled to the nanoelectrode and interfacing with the fluidic channel, the bio-receptor being configured and arranged to chemically interact with target biologically-active molecules in the fluidic channel, and to impart an impedance characteristic to the nanoelectrode that is based upon the chemical interaction with the target molecules;
   an electrical contact electrically connected to the nanoelectrode and isolated from contact with the fluid in the fluidic channel; and
   a clamp including a spring component and configured and arranged to, in response to pressing of the micro-fluidic structure to the bio-sensor, clamp the micro-fluidic structure to the bio-sensor and to, via the clamping and spring force applied via the spring component, form the cavity and a liquid-tight seal that confines the fluid within the cavity.

14. A sensor according to claim 1, wherein the micro-fluidic unit has at least one sidewall that defines the fluid channel with an inlet and an outlet, the fluid channel being configured and arranged with the nanoelectrode to present fluid to the nanoelectrode by flowing the fluid between the inlet and the outlet.

15. The apparatus of claim 13, wherein the bio-receptor is configured and arranged to chemically interact with different types of target molecules, and to impart different impedance characteristics to the nanoelectrode for each of the different types of target molecules.

16. The apparatus of claim 15, wherein
   the bio-receptor includes different types of probe biomolecules, each type of probe biomolecule being coupled to a specific region of the nanoelectrode,
   the nanoelectrode has a plurality of the specific regions each having a different type of the probe biomolecule,
   each specific region is configured and arranged with the type of probe biomolecule coupled thereto, to provide an output indicative of a specific one of the different types of target molecules chemically interacting with the type of probe biomolecule coupled to the specific region.

17. The apparatus of claim 13, further comprising a flex-foil having a deformable bump configured and arranged to make electrical connection with the electrical contact in response to the clamp pressing the micro-fluidic structure to the bio-sensor.

* * * * *